United States Patent
Tsang et al.

(10) Patent No.: US 8,257,332 B2
(45) Date of Patent: *Sep. 4, 2012

(54) ELASTIC COMPOSITE FOR A DISPOSABLE ABSORBENT GARMENT

(75) Inventors: Patrick King Yu Tsang, Tuen Mun (HK); Kuo-Shu Edward Chang, Charlotte, NC (US); Anne Smid, Wolvega (NL); Andrew C. Wright, Derbyshire (GB)

(73) Assignee: DSG Technology Holdings Ltd., Tortola (VG)

( * ) Notice: Subject to any disclaimer, the term of this patent is extended or adjusted under 35 U.S.C. 154(b) by 367 days.

This patent is subject to a terminal disclaimer.

(21) Appl. No.: 12/290,006

(22) Filed: Oct. 24, 2008

(65) Prior Publication Data
US 2009/0124992 A1 May 14, 2009

Related U.S. Application Data

(63) Continuation of application No. 10/733,649, filed on Dec. 11, 2003, now Pat. No. 7,462,172.

(51) Int. Cl.
*A61F 13/15* (2006.01)
*A61F 13/20* (2006.01)

(52) U.S. Cl. ............... 604/385.24; 604/385.27

(58) Field of Classification Search ............. 604/385.24, 604/385.26, 385.27, 391, 392, 385.01
See application file for complete search history.

(56) References Cited

U.S. PATENT DOCUMENTS

| | | |
|---|---|---|
| 1,195,949 A | 8/1916 | Carney |
| 2,718,254 A | 9/1955 | Carlson |
| 2,902,395 A | 9/1959 | Hirschy et al. |
| 3,041,230 A | 9/1962 | Diehl |
| 3,627,621 A | 12/1971 | Mowers |
| 3,800,796 A | 4/1974 | Jacob |
| 3,801,401 A | 4/1974 | Cope et al. |

(Continued)

FOREIGN PATENT DOCUMENTS
EP 1188427 3/2002
(Continued)

OTHER PUBLICATIONS

International Search Report issued Jul. 8, 2008, during the prosecution of International Application No. PCT/US2007/71898. Published Oct. 9, 2008.

(Continued)

*Primary Examiner* — Tatyana Zalukaeva
*Assistant Examiner* — Susan Su
(74) *Attorney, Agent, or Firm* — Albert Q. Amatong, Jr.; The Amatong Law Firm, PLLC

(57) ABSTRACT

An elastic composite is provided in a disposable absorbent garment such as a diaper or training pants. The elastic composite has a base layer, a top layer, and an elastic construction disposed therebetween. The elastic construction includes a plurality of spaced apart (e.g. generally equally spaced apart) elastic elements (e.g. strands or threads) that are aligned in a generally cross machine direction and in generally parallel relation. Further, the top and base layers define a first longitudinally extending side edge and a second longitudinally extending side edge between which, the elastic construction is disposed. The elastic composite further includes an elasticized region, wherein the elastic construction is disposed, a first non-elasticized region disposed between the first side edge and the elasticized region, and a second non-elasticized region disposed between the second side edge and the elasticized region.

18 Claims, 6 Drawing Sheets

U.S. PATENT DOCUMENTS

| | | | |
|---|---|---|---|
| 4,284,454 A | | 8/1981 | Joa |
| 4,527,990 A | | 7/1985 | Sigl |
| 4,642,151 A | | 2/1987 | Coenen |
| 4,726,874 A | | 2/1988 | VanVliet |
| 4,857,067 A | * | 8/1989 | Wood et al. ............... 604/389 |
| 5,004,466 A | * | 4/1991 | Uda et al. ............. 604/385.24 |
| 5,127,981 A | | 7/1992 | Straub et al. |
| 5,242,436 A | | 9/1993 | Weil et al. |
| 5,246,433 A | | 9/1993 | Hasse et al. |
| 5,370,634 A | | 12/1994 | Ando et al. |
| 5,383,871 A | | 1/1995 | Carlin et al. |
| 5,429,694 A | | 7/1995 | Herrmann |
| 5,464,401 A | | 11/1995 | Hass et al. |
| 5,531,729 A | | 7/1996 | Coles et al. |
| 5,531,850 A | | 7/1996 | Herrmann |
| 5,540,796 A | | 7/1996 | Fries |
| 5,591,152 A | | 1/1997 | Buell et al. |
| 5,607,416 A | * | 3/1997 | Yamamoto et al. ........ 604/397 |
| 5,628,741 A | | 5/1997 | Buell et al. |
| 5,669,897 A | | 9/1997 | Lavon et al. |
| 5,685,873 A | | 11/1997 | Bruemmer |
| 5,706,524 A | * | 1/1998 | Herrin et al. ................ 2/400 |
| 5,779,691 A | | 7/1998 | Schmitt |
| 5,807,368 A | | 9/1998 | Helmer |
| 5,807,371 A | | 9/1998 | Toyoda et al. |
| 5,916,207 A | | 6/1999 | Toyoda et al. |
| 5,938,652 A | | 8/1999 | Sauer |
| 6,004,306 A | | 12/1999 | Robles et al. |
| 6,086,571 A | | 7/2000 | Guevara et al. |
| 6,123,694 A | | 9/2000 | Pieniak et al. |
| 6,146,369 A | | 11/2000 | Hartman et al. |
| 6,197,012 B1 | * | 3/2001 | Mishima et al. ........ 604/385.04 |
| 6,313,372 B1 | | 11/2001 | Suzuki |
| 6,336,922 B1 | | 1/2002 | VanGompel et al. |
| 6,340,782 B1 | | 1/2002 | Kling et al. |
| 6,419,667 B1 | | 7/2002 | Avalon et al. |
| 6,425,430 B1 | | 7/2002 | Ward et al. |
| 6,454,750 B1 | | 9/2002 | Vogt et al. |
| 6,454,752 B1 | | 9/2002 | Huang et al. |
| 6,572,595 B1 | | 6/2003 | Klemp et al. |
| 6,649,001 B2 | | 11/2003 | Heden et al. |
| 6,740,071 B2 | * | 5/2004 | Gibbs ....................... 604/392 |
| 6,855,223 B2 | | 2/2005 | Johnson |
| 6,869,494 B2 | * | 3/2005 | Roessler et al. ............ 156/201 |
| 6,967,178 B2 | * | 11/2005 | Zhou et al. .................. 442/149 |
| 7,077,834 B2 | * | 7/2006 | Bishop et al. ........... 604/385.11 |
| 7,101,360 B2 | * | 9/2006 | Sorenson et al. ............ 604/391 |
| 7,201,744 B2 | * | 4/2007 | Van Gompel et al. ........ 604/391 |
| 7,316,840 B2 | * | 1/2008 | Neculescu et al. ........ 428/297.4 |
| 7,361,246 B2 | | 4/2008 | Chang et al. |
| 7,534,481 B2 | * | 5/2009 | Seth et al. ................... 428/80 |
| 7,638,014 B2 | * | 12/2009 | Coose et al. ................ 156/250 |
| 7,708,849 B2 | * | 5/2010 | McCabe .................... 156/73.1 |
| 7,850,673 B1 | * | 12/2010 | Carlbark et al. ............. 604/392 |
| 7,918,961 B2 | * | 4/2011 | Wada et al. ................. 156/259 |
| 2001/0039700 A1 | | 11/2001 | Krueger |
| 2002/0002358 A1 | | 1/2002 | Durrance et al. |
| 2002/0038110 A1 | | 3/2002 | Kusibojoska et al. |
| 2002/0151863 A1 | | 10/2002 | Toyoshima |
| 2002/0177829 A1 | | 11/2002 | Fell et al. |
| 2003/0064652 A1 | | 4/2003 | Heden et al. |
| 2003/0069557 A1 | | 4/2003 | Driskell et al. |
| 2003/0083634 A1 | | 5/2003 | Fernfors |
| 2003/0089454 A1 | | 5/2003 | Johnson |
| 2003/0109844 A1 | | 6/2003 | Gibbs |
| 2003/0139725 A1 | | 7/2003 | Gibbs |
| 2003/0144643 A1 | | 7/2003 | Jarpenberg et al. |
| 2004/0243090 A1 | | 12/2004 | Toyoshima et al. |
| 2005/0095942 A1 | | 5/2005 | Mueller et al. |
| 2005/0131373 A1 | | 6/2005 | Wright et al. |
| 2006/0058767 A1 | | 3/2006 | Zhang et al. |
| 2006/0058768 A1 | | 3/2006 | Zhang et al. |
| 2006/0241560 A1 | | 10/2006 | Chang et al. |
| 2007/0016155 A1 | | 1/2007 | Chang et al. |

FOREIGN PATENT DOCUMENTS

| | | |
|---|---|---|
| EP | 1520569 | 4/2005 |
| JP | 2002-192641 | 7/2002 |
| WO | WO 9519258 A1 | 7/1995 |
| WO | 01/00915 | 1/2001 |
| WO | WO 0232364 A1 | 4/2002 |
| WO | WO/03/041627 | 5/2003 |
| WO | WO 03017903 | 6/2003 |
| WO | WO 2004/087416 | 10/2004 |
| WO | 2005/060910 | 7/2005 |

OTHER PUBLICATIONS

Written Opinion issued Jul. 8, 2008, during the prosecution of International Application No. PCT/US2007/71898. Published Dec. 26, 2008.

Nonfinal Office Action mailed Jan. 27, 2006, during the prosecution of U.S. Appl. No. 10/733,649.

Final Office Action mailed Sep. 15, 2006, during the prosecution of U.S. Appl. No. 10/733,649.

Nonfinal Office Action mailed Jun. 8, 2007, during the prosecution of U.S. Appl. No. 10/733,649.

Nonfinal Office Action mailed Dec. 26, 2007, during the prosecution of U.S. Appl. No. 10/733,649.

International Preliminary Report on Patentability mailed Jun. 22, 2006, during the prosecution of International Application No. PCT/US2004/012832.

International Search Report mailed Oct. 1, 2004, during the prosecution of International Application No. PCT/US2004/012832. Published Jul. 7, 2005.

Written Opinion mailed Oct. 1, 2004, during the prosecution of International Application No. PCT/US2004/012832. Published Jul. 7, 2005.

European Examination Report mailed Mar. 27, 2007, during the prosecution of EP Application No. 04820707.0.

European Examination Report mailed Apr. 18, 2007, during the prosecution of EP Application No. 04820707.0.

Nonfinal Office Action mailed Jun. 16, 2008, during the prosecution of U.S. Appl. No. 11/474,653.

Nonfinal Office Action mailed Sep. 19, 2007, during the prosecution of U.S. Appl. No. 11/113,114.

Final Office Action mailed Mar. 27, 2008, during the prosecution of U.S. Appl. No. 11/113,114.

\* cited by examiner

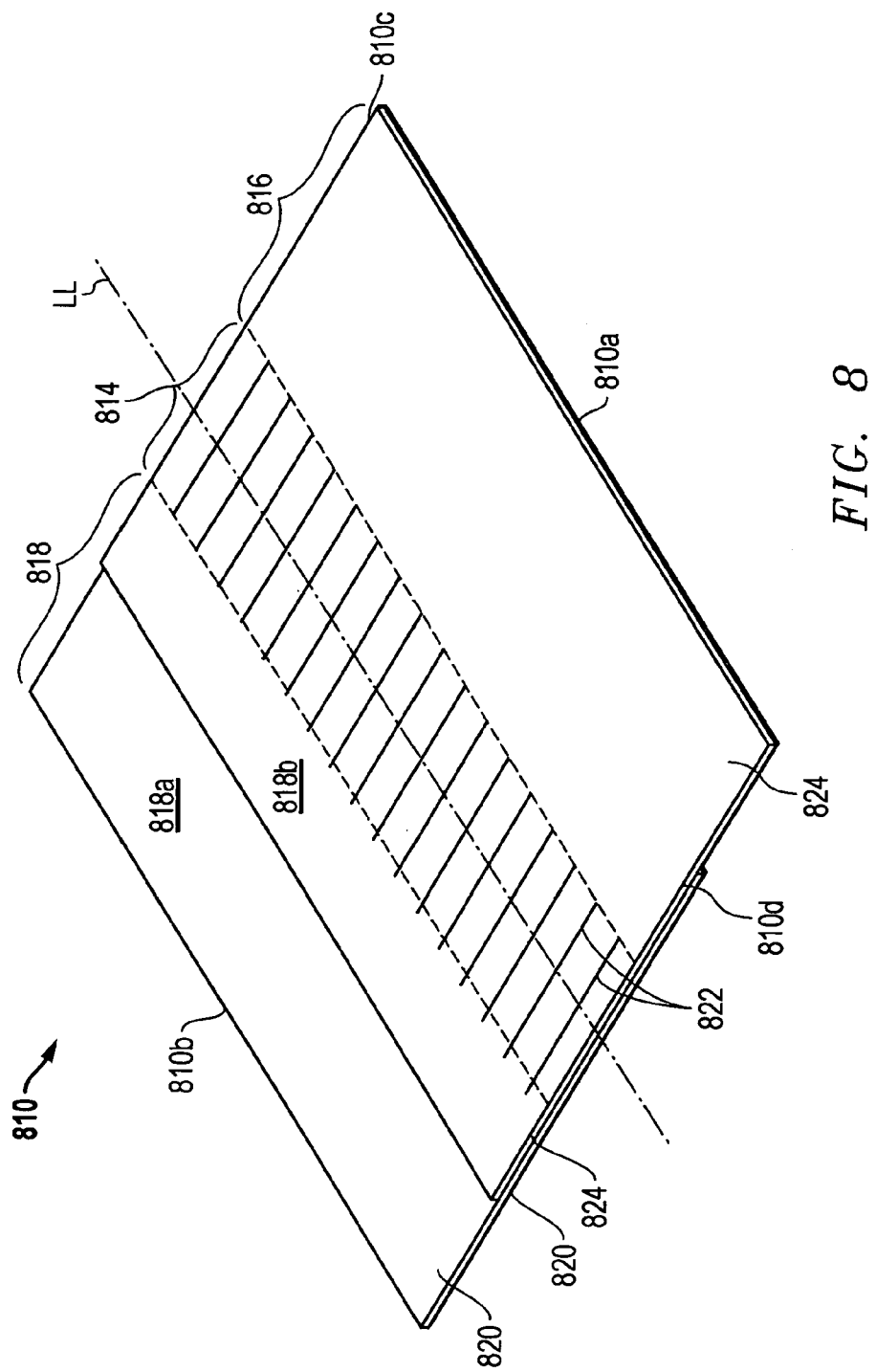

ELASTIC COMPOSITE FOR A DISPOSABLE ABSORBENT GARMENT

The present application claims the benefit of the filing date of U.S. patent application Ser. No. 10/733,649 filed on Dec. 11, 2003 (now pending) (which is hereby incorporated by reference for all purposes and made a part of the present disclosure).

BACKGROUND OF THE INVENTION

The present invention relates generally to disposable absorbent garments or articles such as baby diapers and training pants. More particularly, the present invention relates to an elastic component that can be employed in one or more areas of the garment.

Disposable absorbent garments contemplated by the invention include disposable diapers, disposable pull-on garments, and the like. These garments are worn about the lower torso or waist of the user so as to receive and contain urine and other bodily wastes. The benefits provided by the use of a disposable diaper on an infant are well known and its use has become widespread in the past several decades. Disposable pull-on garments include training pants, pull-on diapers, disposable underwear, and adult incontinence garments. It is generally expected that the user of any one of these garments will be able to put on and take off the garment on his/her own. As for training pants, these garments are used by young children to facilitate the child's transition from using diapers to wearing regular underpants (i.e., during toilet training). Training pants (and other disposable pull-on pants) have closed sides such that the user or caregiver raises the garment about the user's legs to put it on and slips the garment downward about the user's legs to take it off.

The principal elements of a typical disposable absorbent garment include a liquid permeable inner layer (or topsheet), a liquid impermeable outer layer (or backsheet), and an absorbent core sandwiched between the inner and outer layers. Elastic members may be incorporated into different parts of the garment. For example, elastic members may be positioned longitudinally along a diaper, generally outboard of the absorbent core to effect a seal around the buttocks, legs, or both of the users. In addition, several elastic members (e.g., in the form of elongated elastic threads or strands) may be positioned laterally throughout the waist regions (including the side waist regions) of a disposable absorbent garment. The resulting elastication allows the garment to stretch when it is put on and then during wear. In this way, the garment can stretch to accommodate variations in waist size and leg size of the user, while fitting snugly about the waist and legs.

When elastic members are incorporated into a part or area of the garment, that part or area typically becomes a distinct, functional component of the garment. These elastic components include the side panels or ear portions, the waistband, and fastening tabs. The elastic components to which the present invention is directed is generally elongated, and may be a distinct portion of a larger, unitary piece, or a separate, attachable component. Furthermore, the elastic component typically contains one or more sections or layers in addition to the elastic members. In this regard, such an elastic component may be referred to as an elastic composite.

SUMMARY OF THE INVENTION

It is, therefore, one object of the invention to provide an improved disposable absorbent garment, such as a diaper or adult incontinence garment, and further, such a garment incorporating an improved elastic composite as one or more of its components.

For purposes of the present description, the term "elastic band" or "elastic composite" refers to a multi-layer construction of the disposable absorbent garment. In this construction, a plurality of elastic members, such as threads or strands, are disposed adjacent one or more layers, e.g., backsheet and topsheet. In this way, the elastic members imparts elasticity to the adjacent layers and thus, to that part of the disposable absorbent garment. Such an elastic structure may be a distinct attachable component of the garment or may be a distinct portion or section of the garment body or a larger, unitary component of the garment body.

In one aspect of the invention, an elastic composite is provided in a disposable absorbent garment such as a diaper or training pants. The elastic composite has a base layer, a top layer, and an elastic construction disposed therebetween. The elastic construction includes a plurality of spaced apart (e.g. preferably generally equally spaced apart) elastic elements (e.g. strands or threads) that are aligned in generally parallel relation. Further, the top and base layers define a first side edge, a second side edge, and a longitudinal centerline therebetween. The elastic construction is disposed between the two layers and extends in a direction that is between the side edges and is generally parallel with or corresponds to (i.e., overlays) the longitudinal centerline. Further, the elastic elements are oriented along a lateral direction that intersects the side edges and longitudinal centerline (e.g., such that each elastic element is oriented or aligned along a direction that is generally perpendicular to the side edges).

Preferably, the elastic composite includes at least one elasticized region, wherein the elastic construction is disposed, that is spaced inwardly from the side edges and, in some embodiments, positioned generally centrally between the side edges. Such an elastic composite also includes a first non-elasticized region disposed between the first side edge and the elasticized region, and a second non-elasticized region disposed between the second side edge and the elasticized region.

In certain embodiments, the first and second non-elasticized regions provide fastening regions that are generally flat relative to the elastic regions, and may be equipped with a fastening element such as adhesives or a hook or loop element. More preferably, the elastic elements are attached to at least one of the top and base layers such that the elasticized region is shirred when the elastic composite is disposed in a relaxed, un-stretched state. In further embodiments, a second elasticized region is provided between the side edges and a third elasticized region is provided between the first and second elasticized regions.

In preferred embodiments, the elastic construction has a centerline extending therethrough that is spaced generally equidistantly from each side edge and the elastic strands are distributed along this centerline and in generally perpendicular relation therewith. Preferably, the direction of this centerline corresponds with a machine direction of the elastic composite band or more specifically, the web material from which the elastic composite band is cut.

In yet another aspect of the invention, a disposable absorbent garment is provided with a topsheet, a backsheet, and an absorbent core disposed between the topsheet and the backsheet and such that a longitudinal centerline of the garment extends through the topsheet, backsheet, and absorbent core. Together, the topsheet, backsheet, and absorbent core provide a central body of the disposable absorbent garment. The inventive garment further includes an elastic composite band that is attached to the central body. The elastic composite band has a first side edge, a second side edge, and a composite centerline extending in between the side edges. The elastic composite band includes a base layer, a top layer, and an elastic construction disposed between the top and base layers and spaced inwardly from each side edge. The elastic construction includes a plurality of spaced apart elastic elements that are distributed in a direction extending between the side edges and each aligned in generally perpendicular relation with the composite centerline.

Preferably, the elastic composite band includes an elasticized region that is positioned generally centrally between the first and second side edges, and wherein the elasticized region is disposed. The elastic composite also has a first non-elasticized region positioned between the first side edge and the elasticized region, and a second non-elasticized region positioned between the second side edge and the elasticized region. In some embodiments, the elastic composite band is attached adjacent an end of the garment leg (e.g., along a waistline) and provides therealong an elastic waistband on the garment. In further embodiments, the garment has two elastic composite bands each attached along a side margin of the garment. In these embodiments, the elastic composite band provides an elastic waist fastening portion of the diaper, such as an elastic side panel or ear portion of the garment or elastic fastening tab. In one particular embodiment, the elastic composite is provided as the central chassis or central body of the garment.

BRIEF DESCRIPTION OF THE DRAWINGS

FIG. 8 is a perspective view of yet another alternative elastic composite according to the invention.

DETAILED DESCRIPTION OF THE INVENTION

Figure 1:
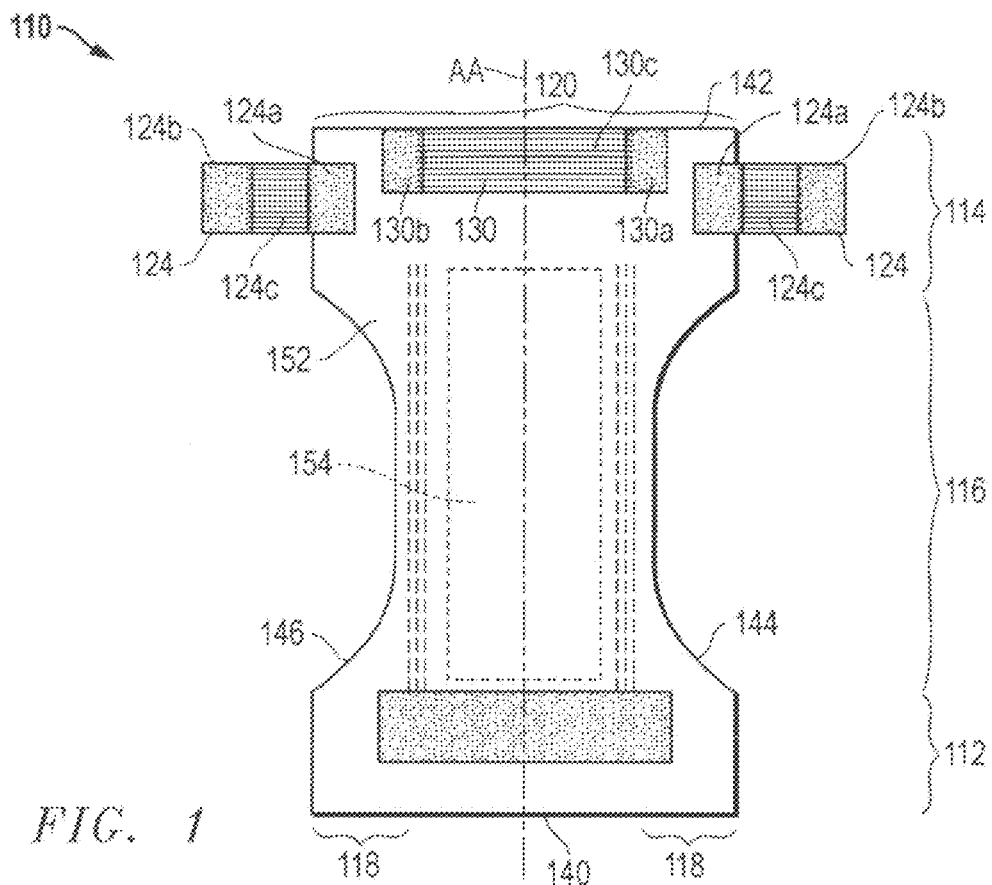
FIG. 1 is a plan view of a disposable absorbent garment in the unfolded configuration; according to the present invention.

Each of FIGS. 1 and 4-9 depict a disposable absorbent garment embodying various aspects of the present invention. More particularly, each of these Figures depict such a garment that incorporates an elastic composite structure or elastic composite in accordance with the present invention. In FIG. 1, a disposable absorbent garment 110 is shown that is suitable for the invention and in the form of a diaper having one or more elastic composites incorporated therein. The elastic composite in FIGS. 1-8 have side and end edges and, thus, may be referred to herein as elastic composite bands.

The disposable absorbent garment 110 in FIG. 1 is of a type that can be placed against or in proximity to the body of a wearer so as to absorb and to contain various bodily exudates. It should be noted, however, that the present invention is applicable to a variety of disposable absorbent articles and garments, including training pants and a variety of adult incontinence products. As will be described below, the inventive elastic composite or elastic composite band may provide a side panel or ear portion, a waistband, a fastening tab or band, or other distinct elastic component of the garment or article. The inventive elastic composite may also be incorporated into an ear portion to elasticate the ear portion or to supplement the ear portion with an elasticated fastening tab. Accordingly, the present invention is not intended to be limited to the structures and the processes specifically described and illustrated herein. For purposes of description, however, the following discussion will be directed to an exemplary disposable diaper only. Moreover, the invention will be described in the context of its various configurations and aspects. It should be appreciated that alternative arrangements of the inventive disposable absorbent garment and such an elastic composite band may comprise various combinations, which include one or more of the various configurations and aspects of the invention.

FIG. 1 is introduced to illustrate some basic features of a disposable diaper 110, most of which are also applicable to other disposable absorbent garments contemplated by the invention. The diaper 110 includes three main regions aligned along an imaginary longitudinal axis or plane AA. These regions include a first waist region 112 (typically at the front of the user when the garment 110 is worn), a back waist region 114, and a crotch region 116. The diaper 110 is also characterized by a front edge 140, a back longitudinal edge 142, a first lateral or side edge or side margin 144, and a second lateral or side edge or side margin 146.

Along a lateral direction, the diaper 110 includes ear regions or ear portions 118 extending laterally from the waist regions 112, 114. Together, the waist regions 112, 114 and crotch region 116 may be referred to as forming a central body portion 120 of the garment 110 that is positioned within side edges 144, 146. The body portion 120 may also be referred to as being formed by a liquid permeable inner layer or topsheet 152, a liquid impermeable outer layer or backsheet (not shown), and an absorbent core 154 sandwiched between the two layers. The ear portions 118 further include fastening tabs 124 for attaching the waist regions 112, 114 together. The diaper 110 also has an elastic waistband 130 positioned generally along the back edge 142 to facilitate fastening and to enhance the fit and seal of the diaper 110. When the hourglass shaped diaper 110 is worn, the crotch region 116 fits about the crotch of the wearer, and the front and back waist regions, 112 and 114, fit about the corresponding waist areas. The ear portions 118, on the other hand, wrap about the wearer and the fastening tabs 124 engage to form a complete, all-around waistline of the diaper 110.

Figure 2A:
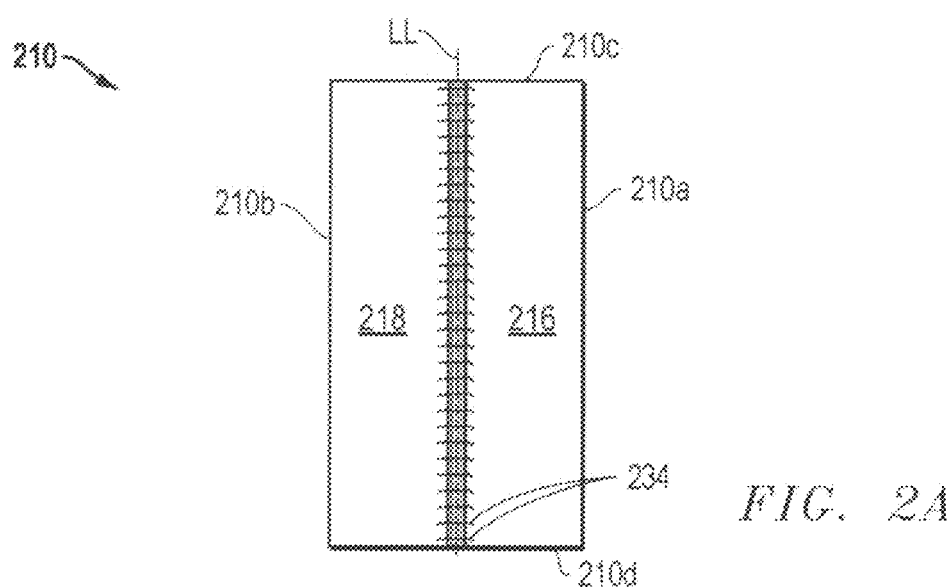
FIG. 2A is a plan view of an elastic composite according to the present invention.
Figure 3:
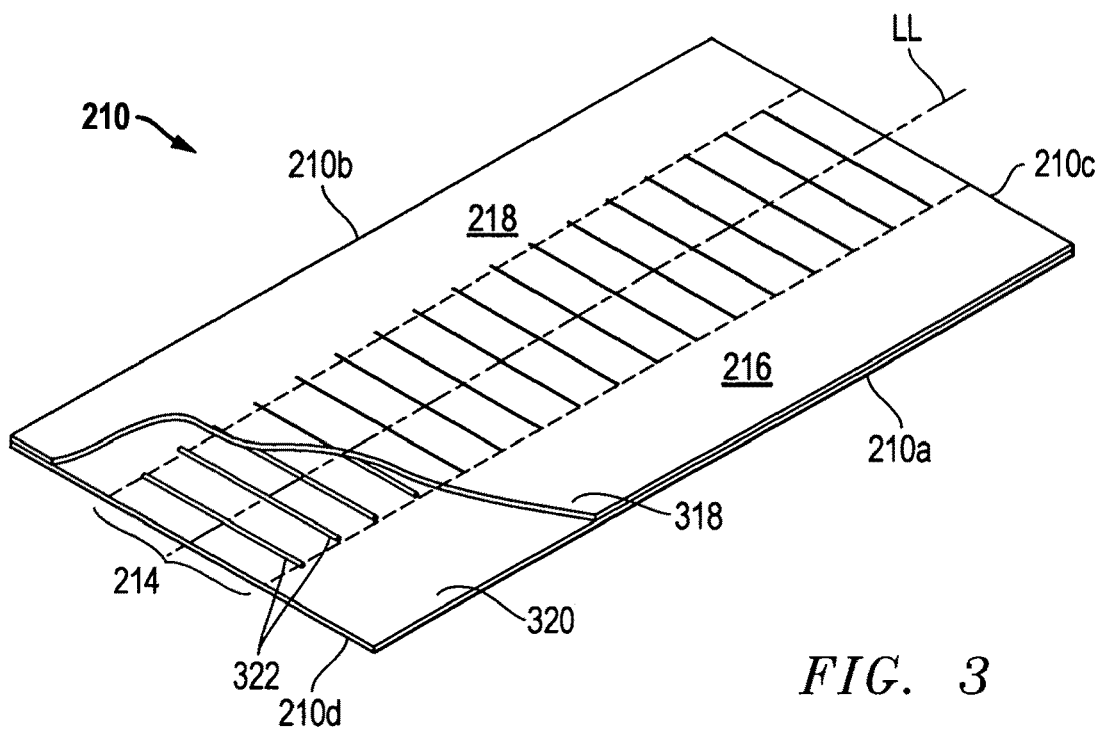
FIG. 3 is a perspective view of the elastic composite of FIG. 2A with a cut-out detail to show an elastic construction.

FIG. 2A depicts a typical elastic composite band 210 according to the invention. More particularly, the elastic composite band 210 is one particularly suited for use as a side panel or fastening tab of a disposable absorbent garment (see, e.g., FIG. 1). FIG. 3 provides a perspective view and partial cut-out of the elastic composite band 210. The elastic composite band 210 may be characterized by an imaginary centerline LL. In one aspect of the invention, the centerline LL preferably corresponds with the machine direction of the elastic composite band 210 during manufacture. The elastic band 210 also has side or longitudinally extending side edges 210a and 210b and laterally extending end edges 210c and 210d. In FIG. 1, the elastic composite band 210 is shown in the stretched state as, for example, when a garment incorporating the elastic composite band 210 is worn. In this state, the elastic composite band 210 stretches, in the lateral or cross-machine direction (denoted by arrows XX).

As used herein, the term "machine" direction refers to the direction at which the component, or more particularly, the material web from which the elastic composite is derived (e.g., cut from) is driven in an assembly line during manufacturing. The term "cross-directional machine direction" or "cross-directional," on the other hand, refers to the direction that is perpendicular to the machine direction. With reference to the elastic composite 20 of FIG. 2, the cross machine direction is the direction XX extending laterally or perpendicularly relative to the longitudinal line LL.

The elastic composite band 210, according to the invention, has a central region 214 in which an elastic construction is situated. Extending laterally from this central elastic or elasticized region 214 are regions 216 and 218, which are substantially non-elasticized. As shown in FIG. 2A, the regions 216, 218 occupy the expanse between the central elastic region 214 and the side edges 210a, 210b. Now with reference to FIG. 3, the elastic composite band 210 has a top layer 318 and a bottom or base layer 320. The two layers 318, 320 preferably extend the total width and length of the elastic composite band 210, thereby providing the side edges 210a, 210b, and the end edges 210c, 210d. Both the base layer 320 and the top layer 318 are preferably a non-woven, breathable, disposable material such as propylene, non-woven fabric, breathable polyethylene/polypropylene films, or non-porous films (or combinations of these materials). The base layer 320 and top layer 318 adhere to one another, thereby sandwiching and securing a plurality of elastic strands 322 therebetween.

The elastic strands 322 may be substituted, in alternative embodiments, by suitable elastic elements such as elastic strands, threads, ribbons, and elastic glue beads. In one aspect of the invention, the elastic elements or strands 322 are distributed along a direction that extend between the side edges 210a, 210b and parallel with (or corresponding to) center line LL. Further, each elastic element 322 is generally aligned or oriented in a direction corresponding with the lateral or cross-machine direction, i.e., in a direction generally perpendicular to the longitudinal center line LL and intersecting the side edges 210a, 210b. Preferably, the strands 322 are disposed in generally parallel relation and spaced apart generally equally along the longitudinal direction. More preferably, the elastic strands 322 are of generally equal length. Accordingly, when the elastic composite band 210 is worn, the strands 322 impart elasticity into the structure which allows the band 210 to stretch in the lateral or cross-machine direction XX.

Figure 2B:
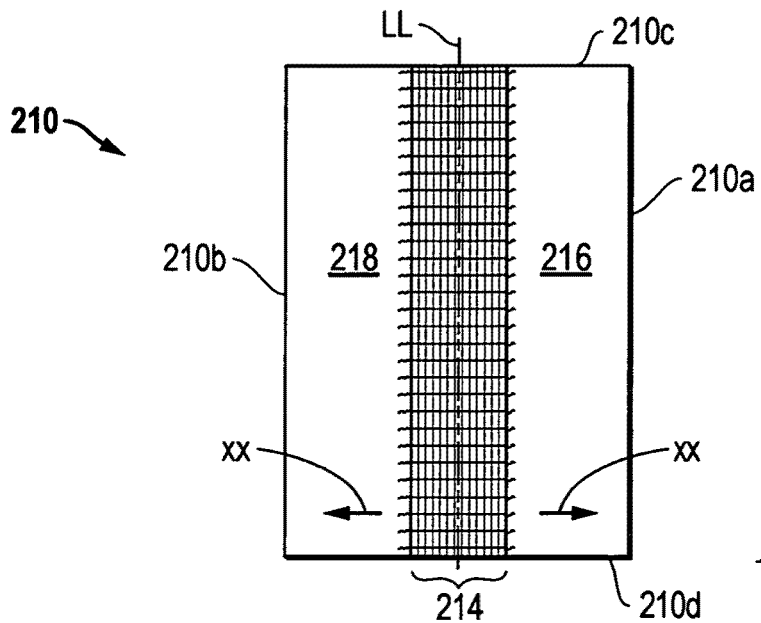
FIG. 2B is a plan view of the elastic composite of FIG. 2A shown in an extended, stretchable condition.

The elastic strands 322 are preferably tensioned during securement between the top and base layers 318, 320. FIG. 2B illustrates the elastic composite band 210 in a laterally stretched condition. In this condition, the central elastic region 214 has a width that is almost equal to the non-elasticized zones 216 and 218. When returned to the non-laterally stretched or relaxed condition, as shown in FIG. 2A, the central elastic region 214 contracts and crimps to a substantially reduced width. In this condition or state, the contracted elastic strands 322 shirrs the elastic composite 210 and provide pleats 234 in the contracted elastic region 214.

The elastic composite band 210 may originate from a web of material that is wound onto spools or festooned. Typically, the user of such material will cut the material to a length required of a particular application. In some applications, one such web of material may provide the source of multiple components of the inventive disposable absorbent garment.

Returning to FIG. 1, the inventive disposable absorbent garment 110 employs one or more elastic composite bands according to the invention, as described above. The disposable absorbent garment 110 employs in each of the ear portions 118, a fastening tab 124 having the inventive elastic composite construction. As the fastening tab 124, the elastic composite band is configured such that one non-elasticized region 124a is attached to and overlaps the central body 120 of the garment 110 while a second non-elasticized region 124b is situated outboard of the side margins 144, 146. An elasticized region 124c, as shown in FIG. 1, provides elasticity, and thus, stretch in the lateral or cross-machine direction (of the elastic composite). In respect to the rest of the garment 110, the elasticity or stretch provided by the central elastic region 124c directed along a direction that is generally perpendicular to the longitudinal center line AA of the garment 110, and corresponds with a direction that wraps about the waistline of the user.

The disposable absorbent garment 110 in FIG. 1 also provides an elastic composite, according to the invention, as the waistband 130. The waistband 130 is situated centrally in the waist region 114. Further, the elastic composite waistband 130 is disposed such that non-elasticized regions 130a, 130b are positioned outwardly of the longitudinal line AA of the garment 110, while an elasticized region 130c is positioned centrally across the longitudinal center line AA. Moreover, the elasticized region 130c is configured such that the elastic strands are aligned or oriented in a direction that is generally perpendicular to the longitudinal center line AA. In this way, the elastic composite waistband 130 imparts elasticity about the waist region 114 of the garment 110, and in a direction corresponding with the direction of waistline about the user.

Figure 4:
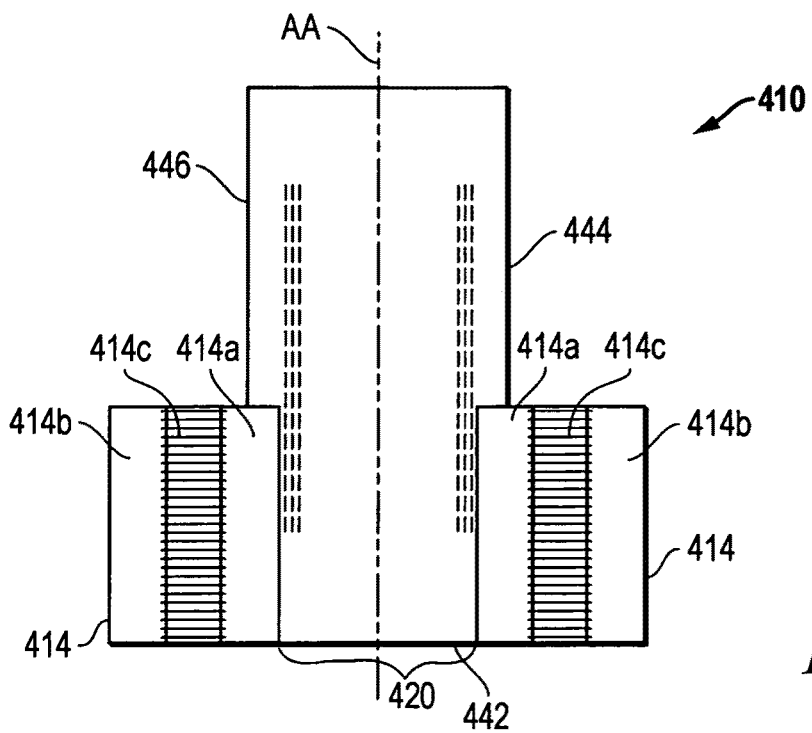
FIG. 4 is a plan view of an alternative disposable absorbent garment according to the invention.

FIG. 4 depicts an alternative disposable absorbent garment 410 according to the invention. Specifically, FIG. 4 depicts a disposable absorbent garment 410 employing elastic composites according to the invention as attachable ear portions or side panels 414. The elastic composite side panels 414 are separate components that are attached to a central body 420 of the garment 410. The elastic composite side panels (or ear portions) 414 are attached near one waist edge 442 of the garment 410 and such that the centerline AA of the side panel 414 is generally parallel with the longitudinal centerline AA of the garment 410. Moreover, each of the elastic composite side panels 414 has a non-elasticized region 414a that is positioned outboard of the side margins 446 of the garment 410 and a second non-elasticized region 414b that is attached inboard of the side margin 446 (or side margin 444). Thus, a central elastic region 414c is situated outboard of the side margin 446 and not directly attached thereto. When the garment 410 is in use, the central elasticized region 414a allows the side panel to stretch in a lateral or cross-machine direction that corresponds with the lateral direction relative to the longitudinal centerline AA of the garment 410. Accordingly, when the garment 410 is worn, the elastic side panel 414 allows for stretching about the waistline of the user.

Figure 5:
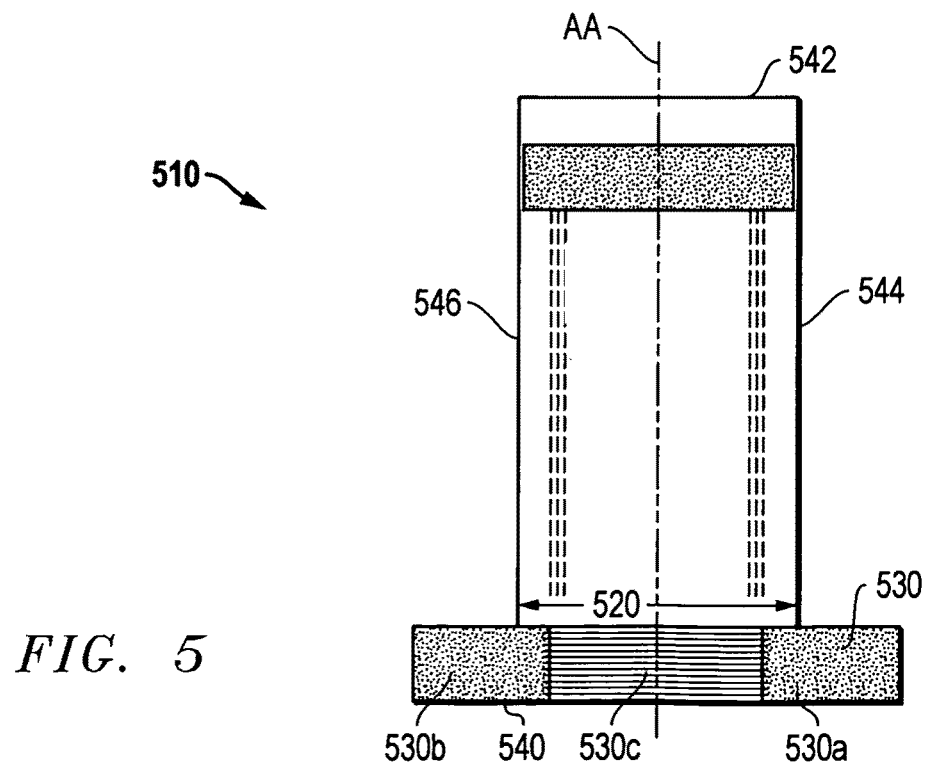
FIG. 5 is a plan view of another alternative disposable absorbent garment, according to the invention, incorporating an elastic composite as a waistband.

FIG. 5 depicts yet another alternative embodiment of a disposable absorbent garment 510 according to the invention. The disposable absorbent garment 510 is a diaper partially defined by end or waist edges 540, 542 (not shown) and side margins 544, 546. Further, the inventive disposable garment 510 has a central body 520 and a separate, attachable elastic waistband 530. Similar to the garments 110, 410 in FIGS. 1 and 4, respectively, the garment 510 employs an elastic composite, as the elastic waistband 530. The inventive elastic waistband 530 is attached adjacent a waist edge 542 of the garment 510 and is positioned centrally about the longitudinal centerline AA. The elastic composite waistband 530 is situated such that non-elasticized regions 530a, 530c extend laterally past the side margins 544, 546, respectively. The central elasticized region 530c is positioned centrally within the central body 520 and side margins 544, 546. The elastic strands of the central elastic region 530c is further situated such that the elastic region 530c provides elasticity or stretch in a lateral direction relative to longitudinal centerline AA. Again, in this way, the elastic composite waistband 530 according to the invention allows for the garment to fit snugly and effectively about the waistline of the user.

Figure 6:
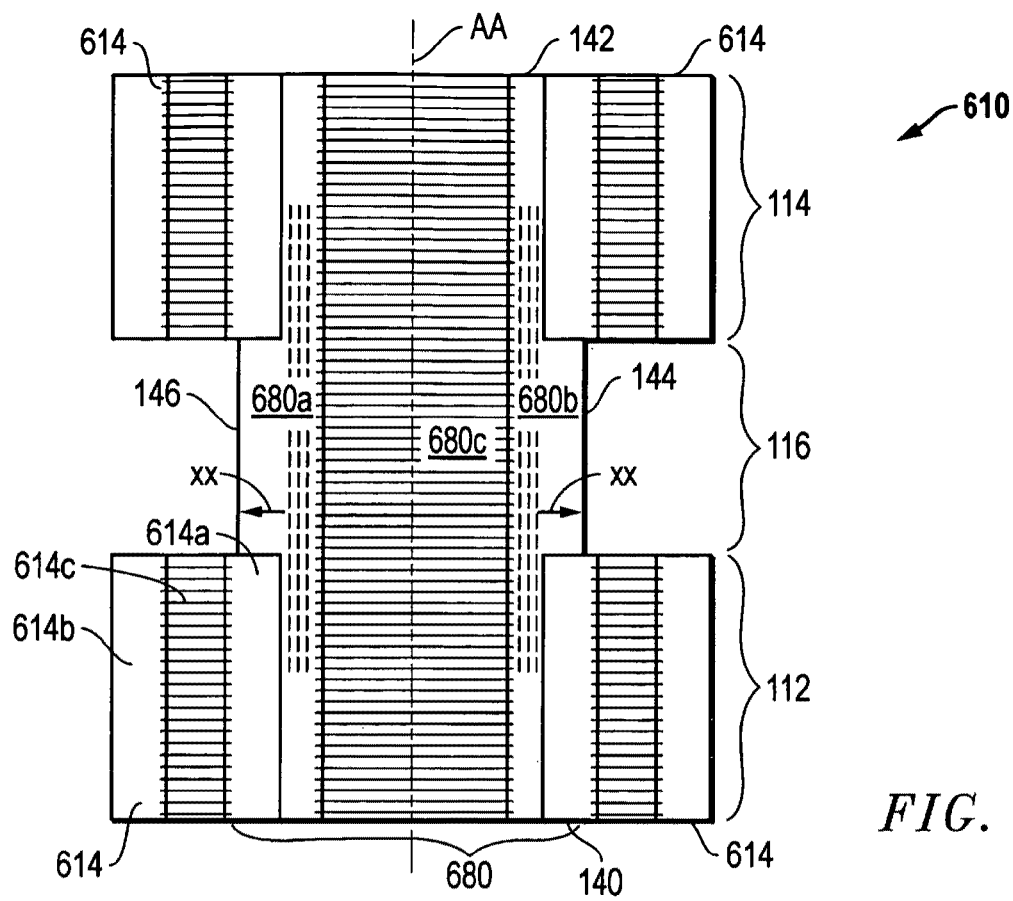
FIG. 6 is a plan view of yet another alternative disposable absorbent garment, according to the invention, further incorporating an elastic composite as a central body chassis.

FIG. 6 illustrates an alternative disposable absorbent garment 610, according to the invention (wherein like reference numerals are used to indicated like elements), in which the inventive elastic composite band is incorporated into various areas or as various garment components. The garment 610 has a front waist region 112, a back waist region 114, and a crotch region 116 positioned therebetween. As with the garment 410 of FIG. 4, an elasticized composite band 614 is attached to each side margin 144, 146, near end edge 140, as an elasticized side panel 614. A second pair of elastic composite bands is attached as an elasticized side panel 660 along the opposite end edge 42 of the garment 610.

FIG. 6 also illustrates the use of the inventive elastic composite band to provide an elasticized central body or chassis 680 at or beneath the crotch region 116 of the garment 610 and in support of an absorbent core (not shown so as to clearly display the chassis 680). The absorbent core is preferably adhered to and movable with the elasticized chassis 680. Thus, the core is preferably a conformable (changes shape in accordance with an outside force), elastic, or extensible (e.g., pulled and permanently stretched) body, as is generally known in the art. In this way, the main or central body of the garment 610 is elasticized in a lateral direction XX that is generally perpendicular to a longitudinal centerline AA of the garment 610. In the garment 610 of FIG. 6, the inventive composite band provides the entire length of the central body or chassis 680. The elastic composite chassis 680 has an elasticized region 680c situated between two non-elasticized regions 680a, 680b. Preferably, the elasticized region 680c provides an elastic construction of a plurality of elastic strands as disclosed previously in respect to the embodiments of FIGS. 1-5. In the illustrated embodiment, the elasticized region 680c extends between end edges 140, 142, thereby imparting lateral elasticity (stretchability) across the entire garment length.

Figure 7:
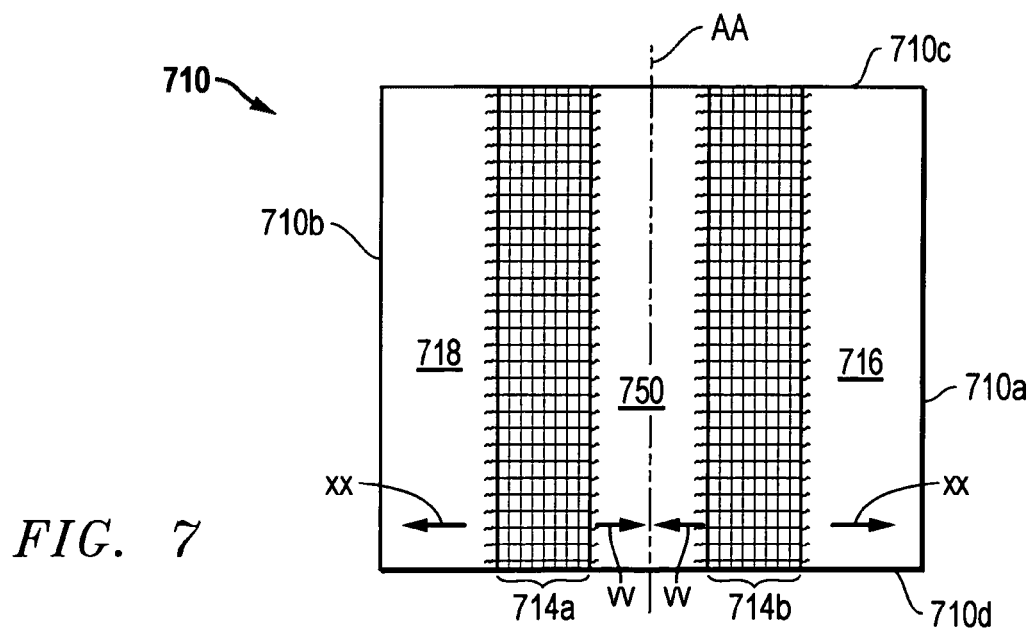
FIG. 7 is a plan view of an alternative elastic composite according to the present invention.

FIG. 7 depicts an alternative embodiment of an elastic composite band according to the present invention. The elastic composite band 710 illustrated therein differs from the previously described elastic composite band (see e.g. FIGS. 2 and 2a) in that the elastic composite band 710 includes two elasticized regions 714a and 714b. The elasticized region 714a, 714b are preferably equidistantly spaced apart on either side of the longitudinal centerline AA. The spacing of the elasticized regions 714a, 714b creates right and left non-elasticized or dead regions 716, 718, as well as central non-elasticized region 750. The elasticized regions 714a, 714b imparts elasticity to elastic composite band 710a in the lateral directions XX, and in the central non-elasticized region 750, also in the opposite lateral direction VV.

FIG. 8 depicts yet another embodiment of an elastic composite band 810 according to the invention. The inventive elastic composite band 810 has, as in previously described embodiments, a central elastic or elasticized region 814 and regions 816 and 818 that are substantially nonelasticized and extend laterally from the central elasticized region 814. The elasticized region 814 is again comprised of a plurality of elastic strands 322 that are disposed in generally parallel relation, and generally perpendicular with a longitudinal centerline LL of the elastic composite band 810 (and the elasticized region 814). The elastic composite band 810 also has end side edges 810a, 810b, and end edges 810c, 810d.

In yet another aspect of the invention, the elastic composite band 810 is further comprised of base layer 820 and top layer 824. As shown in FIG. 8, base and top layers 820, 824 sandwich the elastic strands 822 therebetween. In contrast to previously described embodiments, layers 820 and 824 are offset in respect to one another. Specifically, the two layers 820, 824 are not positioned squarely or evenly one atop another, but overlap. In this way, the elastic composite band 810 is made wider. In particular, by offsetting the two layers 820, 824, the nonelasticized regions 816, 818 are extended and may be referred to as having an outside section (e.g., 818a) formed by one of the layers 820, 824 and an inside section (e.g., 818b) having both a top and a bottom layer 820, 824. Preferably, the two layers 820, 824 are two plies of nonwoven material. The wider nonelasticized, nonwoven regions 816, 818 provide a working area on which fastening materials and other accessories or structural attributes of the disposable absorbent garment may be situated. In various embodiments, the offset or overlap of the two layers 820, 824 may be varied so as to create nonelasticized regions 816, 818 of various widths. Moreover, a wider elastic composite band (and specifically, nonelasticized regions of the elastic composite band) is attained, without increasing the size of the nonwoven layers.

Figure 9A:
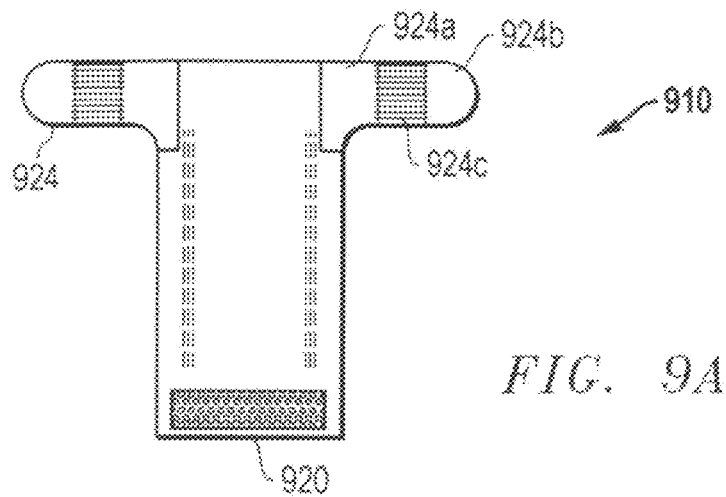
FIGS. 9A-9C are plan view of a further alternative disposable absorbent garments, according to the invention.
Figure 9B:
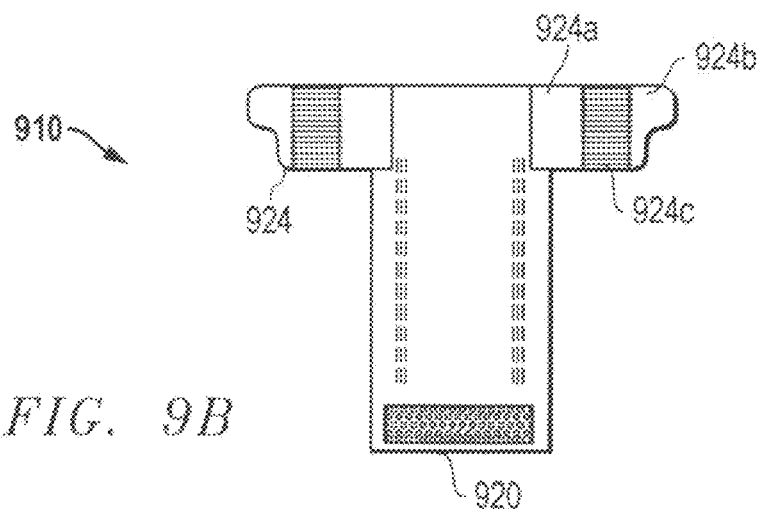
Figure 9C:
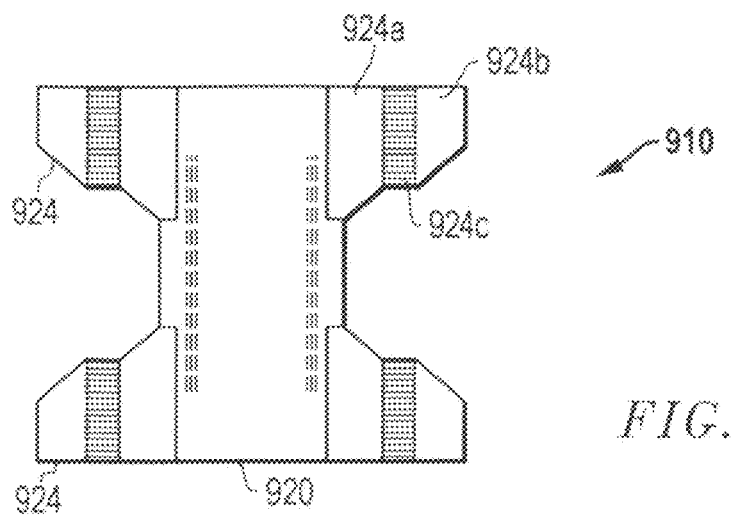

FIGS. 9A-9C are provided to illustrate further embodiments of the present invention. More specifically, FIGS. 9A-9C provide alternate designs, specifically alternate shapes, of the inventive elastic composite band. In these figures, like elements are referenced using like numerals.

Referring to FIGS. 9A and 9B, a disposable absorbent garment 910 is shown having a central body 920 and elastic composite bands in the form of ears or side panels 924. The ears 924 have inner and outer nonelasticized regions 924a, 924b, and a central elasticized region 924c situated therebetween. These two figures illustrate an elastic composite band according to the invention having nonelasticized regions 924a and 924b that are different from one another and do not provide side edges of the elastic composite band 924 which are in generally parallel relation. In both designs, the side edge of the outer nonelasticized regions 924b are rounded or curved. The shape of the elastic composite bands 924 in these two figures provide, among other advantages, a more attractive product as perceived by the consumer.

Now turning to FIG. 9c, yet another variation of the elastic composite band 924 is shown applied to a training pants 910. Specifically, the inventive elastic composite band 924 has nonelasticized regions 924a and 924b of different geometries. This design of the elastic composite bands 924 provide an aesthetic as well as a functional advantage. The functional advantage comes in the form of an improved fit around the wearer's leg, particularly due to the shape of the elastic composite band 924.

The foregoing description of the present invention has been presented for purposes of illustration and description. It is to be noted that the description is not intended to limit the invention to the various apparatus and processes disclosed herein. Various aspects of the invention as described above, may be applicable to other types of disposable absorbent articles and garments, and processes for making the same. For example, the elastic composite described above, may be incorporated in other disposable absorbent garments such as training pants, etc. or in other areas or as other components of the garment. Such variations of the invention will become apparent to one skilled in the relevant consumer products art provided with the present disclosure. Consequently, variations and modifications commensurate with the above teachings, and the skill and knowledge of the relevant art, are within the scope of the present invention. The embodiments described and illustrated herein are further intended to explain the best modes for practicing the invention, and to enable others skilled in the art to utilize the invention and other embodiments and with various modifications required by the particular applications or uses of the present invention.

What is claimed is:

1. In a disposable absorbent garment, an elastic composite comprising:
    a base layer;
    a top layer;
    an elastic construction disposed therebetween, said elastic construction including a plurality of spaced apart elastic elements aligned in generally parallel relation;
    wherein said top and base layers define a first side edge, a second side edge, a first end edge, a second end edge, and a longitudinal centerline extending between said side edges in a direction intersecting said first and second end edges, said elastic construction being disposed between said top and base layers and extending between said side edges in a direction generally parallel with or corresponding to said longitudinal centerline; and
    wherein each said elastic element is generally aligned laterally along a cross-machine direction of said elastic composite and oriented along a direction intersecting said longitudinal centerline and said side edges and
    wherein each said elastic element is spaced apart and disconnected from other elastic elements of the elastic construction; and
    wherein said elastic construction extends generally uniformly from said first end edge to said second end edge, and such that each end edge is formed, at least partly, by an edge of the base layer and an edge of the top layer, and an elastic element is situated proximate said end edges;
    an elasticized region spaced inwardly from said side edges, said elastic construction being disposed in said elasticized region;
    a first non-elasticized region free of said elastic elements disposed between said first side edge and said elasticized region; and
    a second non-elasticized region free of said elastic elements disposed between said second side edge and said elasticized region; and
    wherein each said elastic element extends from one elastic element end located proximate the first non-elasticized region to another elastic element end located proximate the second non-elasticized region.

2. The elastic composite of claim 1, wherein said elastic elements are elastic strands.

3. The elastic composite of claim 1, wherein said first and second non-elasticized regions provide fastening regions that are generally flat relative to said elastic region.

4. The elastic composite of claim 3, wherein at least one of said first and second non-elasticized regions is equipped with a fastening element.

5. The elastic composite of claim 4, wherein said fastening element is selected from the group of fastening elements consisting of: adhesive elements and hook and landing elements.

6. The elastic composite of claim 1, wherein said elastic elements are attached to at least one of said top and base layers such that said elasticized region is shirred when said elastic composite is disposed in a relaxed, un-stretched state.

7. The elastic composite of claim 1, further comprising:
    a second elasticized region disposed between said side edges, said second elasticized region including a second elastic construction having a plurality of spaced apart elastic elements aligned in generally parallel relation, the second elastic construction being disposed between the top and base layers;
    wherein each said elastic element of the second elastic construction is generally aligned laterally along a cross-machine direction of the elastic composite and oriented along a direction intersecting said longitudinal centerline and said side edges; and
    a third non-elasticized region free of said elastic elements of said first and second elastic constructions disposed between said first and second elasticized regions.

8. The elastic composite of claim 1, wherein said elastic elements are spaced inwardly from said side edges and aligned in generally perpendicular relation with a longitudinal centerline of said elastic composite.

9. In a disposable absorbent garment, an elastic composite comprising:
    a base layer;
    a top layer; and
    an elastic construction including a plurality of spaced apart elastic elements;
    wherein said top layer and said base layer are disposed to sandwich said elastic construction therebetween and to define a first lateral side edge of said elastic composite, a second lateral side edge of said elastic composite, a first end edge of the elastic composite; a second end edge of the elastic composite, and wherein said elastic construction extends generally along a longitudinal direction spaced inwardly from said side edges and corresponding to a machine direction of said elastic composite, said elastic elements extending in generally lateral relation with said longitudinal direction; and
    wherein said elastic construction provides an elastic region spaced inwardly from said first and second side edges and extends from said first end edge to said second end edge, such that each end edge is formed, at least partly, by an edge of the top layer and an edge of the bottom layer, and an elastic element is situated proximate said end edges; and
    a first non-elasticized region free of said elastic elements disposed between said first side edge and said elasticized region; and
    a second non-elasticized region free of said elastic elements disposed between said second side edge and said elasticized region;
    wherein each said elastic element extends from one elastic element end located proximate the first non-elasticized region to another elastic element end located proximate the second non-elasticized region.

10. The elastic composite of claim 9, wherein said elastic elements are disposed such that said elastic construction provides a generally laterally elasticized elastic region.

11. The elastic composite of claim 9, wherein said first and second non-elasticized regions provide fastening regions that are generally flat relative to said elasticized region.

12. The elastic composite of claim 9, wherein said elastic elements are oriented in generally perpendicular relation with said longitudinal direction.

13. The elastic composite of claim 9, wherein said plurality of elastic elements include a plurality of spaced apart disconnected elastic elements.

14. The elastic composite of claim 13, wherein said plurality of elastic elements are spaced in mutually generally parallel relation and disposed across a longitudinal centerline of said elastic composite and wherein each elastic element is spaced apart and disconnected from other elastic elements.

15. The elastic composite of claim 9, wherein said first and second lateral side edges have portions that are not in parallel relation.

16. The elastic composite of claim 15, wherein said first non-elasticized region defines a geometry different from a geometry defined by said second non-elasticized region.

17. The elastic composite of claim 15, wherein said first lateral side edge has a rounded or curved portion.

18. In a disposable absorbent garment, an elastic composite comprising:
- a first lateral side edge, a second lateral side edge spaced from said first side edge, a first end edge extending between said side edges, a second end edge extending between said side edges and spaced from said first end edge, and a longitudinal centerline spaced inwardly from said side edges and extending in a direction intersecting said first and second end edges;
- a base layer;
- a top layer; and
- an elastic construction including a plurality of spaced apart elastic elements aligned in generally parallel relation and disposed between said top layer and said base layer, said elastic construction being spaced inwardly from said side edges and extending between said side edges in a direction generally parallel with or corresponding to said longitudinal centerline to define an elasticized region spaced inwardly from said side edges, a first non-elasticized region free of said elastic elements disposed between said first side edge and said elasticized region, and a second non-elasticized region free of said elastic elements disposed between said second side edge and said elasticized region;

wherein each said elastic element is oriented along a direction intersecting said longitudinal centerline and said side edges and extends generally laterally from one elastic element end located proximate the first non-elasticized region to another elastic element end located proximate the second non-elasticized region; and wherein said elastic construction extends from said first end edge to said second end edge, such that each end edge is formed, at least partly, by an edge of the base layer, an edge of the top layer, and an elastic element is situated proximate said end edges.

* * * * *